United States Patent [19]

Ureche

[11] Patent Number: 5,112,300
[45] Date of Patent: May 12, 1992

[54] METHOD AND APPARATUS FOR CONTROLLING ULTRASONIC FRAGMENTATION OF BODY TISSUE

[75] Inventor: Alexander Ureche, El Toro, Calif.

[73] Assignee: Alcon Surgical, Inc., Fort Worth, Tex.

[21] Appl. No.: 503,666

[22] Filed: Apr. 3, 1990

[51] Int. Cl.$^5$ .............................................. A61B 17/00
[52] U.S. Cl. ................................ 604/22; 128/24 AA; 310/323
[58] Field of Search ...................... 604/22, 27; 606/39, 606/45, 128, 167, 169, 170, 171, 166; 128/24 A, 48, 49, 751, 752, 755; 310/323, 325

[56] References Cited

U.S. PATENT DOCUMENTS

| | | | |
|---|---|---|---|
| 3,131,515 | 5/1964 | Mason | 310/325 |
| 3,589,363 | 6/1971 | Banko et al. | 604/22 |
| 3,693,613 | 9/1972 | Kelman . | |
| 3,990,452 | 11/1976 | Murry et al. | 606/169 |
| 4,032,803 | 6/1977 | Durr et al. . | |
| 4,223,676 | 9/1980 | Wuchinich . | |
| 4,526,571 | 7/1985 | Wuchinich . | |
| 4,634,419 | 1/1987 | Kreizman et al. | 604/22 |
| 4,691,724 | 9/1987 | Garcia et al. | 134/169 R |
| 4,713,051 | 12/1987 | Steppe et al. . | |
| 4,750,488 | 6/1988 | Wuchinich et al. | 606/128 |
| 4,750,902 | 6/1988 | Wuchinich . | |
| 4,869,715 | 9/1989 | Sherburne | 604/22 |
| 4,886,060 | 12/1989 | Wiksell | 128/24 A |

Primary Examiner—Stephen C. Pellegrino
Assistant Examiner—Steven J. Shumaker
Attorney, Agent, or Firm—James Arno; Sally Yeager; Christopher Brody

[57] ABSTRACT

This invention is related to an improved method and apparatus for use in controlling the ultrasonic fragmentation of the body tissue. The ultrasonic apparatus includes a transducer assembly mounted in the handpiece assembly. The transducer is operable for converting electrical power to ultrasonic mechanical vibrational energy. A vibrational amplifying device is coupled to the transducer assembly and includes in series asymmetrical horn and symmetrical horn portions. Included in one of the horn portions is an operative tip.

7 Claims, 4 Drawing Sheets

METHOD AND APPARATUS FOR CONTROLLING ULTRASONIC FRAGMENTATION OF BODY TISSUE

BACKGROUND OF THE INVENTION

This invention relates generally to an improved ultrasonic surgical apparatus for enhancing tissue fragmentation.

Ultrasonic surgical apparatus and aspirators have gained widespread acceptance in the microsurgical field. They have been used successfully for the fragmentation and removal of body tissue. Essentially, an apparatus of this type includes an ultrasonic transducer housed in a handpiece. Such ultrasonic transducers are operable for converting electrical energy supplied thereto into high velocity vibrational movements. The transducer generated ultrasonic vibrations are transmitted to a surgical operative tip that is coupled thereto.

In cataract surgery, for example, the operative tip is insertable through a small incision formed in the eye and is manipulated so as to actually contact the cataractous lens. Ultrasonic vibrations cause the lens to fragment. The tissue fragments and other body fluids including irrigation fluid are aspirated from the surgical site by an aspiration system that includes an aspiration passage extending through the operative tip. The aspiration is established by an external vacuum pump located on an external control device. The fragmentation of the lens is the result of cutting action introduced by the vibrating tip and the disruptive cavitation developed by the intense ultrasonic field adjacent the operative tip. Known prior art ultrasonic devices, such as described in U.S. Pat. No. 4,750,902, tend to produce high cutting displacement at the operative tip. However, uncontrolled cavitation especially in ophthalmic surgical procedures, such as cataract surgery, can lead to a variety of problems including inefficient and prolonged fragmentation. Efficient fragmentation is, however, desirable because it reduces the size of the tissue particles entering the aspiration passageway. Since these aspiration passageways are relatively small (e.g., 2 mm) it is important to avoid occlusion or blockage thereof. Occlusion also has other drawbacks since it tends to create significant negative pressure in the aspiration system. Moreover, uncontrolled cavitation creates a degree of turbulence motion in the eye which draws fragmented tissue particles longitudinally away from the tip opening. As a consequence, the efficiency of the fragmentation and aspiration are diminished. Furthermore, the swirling bubble action created by cavitation has a tendency to obscure or cloud the visibility around the operative site so as to hinder the physician during the operation. Moreover, cavitation can be produced by tool portions such as the tip nut or other sections of the ultrasonic horn and can lead to an unnecessary waste of power.

Ultrasonic surgical devices of the kind discussed above are usually operated at relatively high mechanical displacement. High mechanical displacement generates heat any time a frictional force has to be overcome. Most of the frictional losses are generated within the threads used to couple different sections of the handpiece. It is common practice to use threads for coupling the tip with the horn and to use a threaded bolt for compressing the piezoelectric elements between two metal cylinders in a sandwich-type configuration. If those threads are placed in a high vibrational displacement area then we should expect temperature increases especially if the fluid flow stops due to an occlusion. Besides several ultrasonic surgical aspirators utilize low frequency (i.e., below 40 KHz) which only enhances cavitation and thus eye turbulence.

However, in certain instances it is desired to maximize the vibrational displacement of the operative tip. In such situations it is desirable for reasons including safety to minimize the electrical power applied to the handpiece.

SUMMARY OF THE INVENTION

According to the present invention there are provided an improved method of and apparatus for controlling the fragmentation of body tissue of the eye.

There is disclosed an ultrasonic apparatus comprising a handpiece assembly. The apparatus includes transducer means mounted in the handpiece assembly and being operable for converting electrical power to ultrasonic mechanical vibrational energy.

In an illustrated embodiment, motion amplifying means are provided and is acoustically coupled at one end thereof to the transducer means. The amplifying means includes an operative tip portion at another end thereof for contacting body tissue to be removed. The amplifying means includes a symmetrical step horn portion and an asymmetrical step horn portion being connected in series with each other. The operative tip portion is connected to one of the horn portions and is operable for providing a desired degree of displacement at a distal end segment thereof.

In an illustrated embodiment, the operative tip portion is part of the symmetrical horn portion and provides substantially zero displacement at its proximal end segment and maximum displacement at a distal end segment thereof. A body or asymmetrical portion is connected to the symmetrical horn portion does not substantially amplify displacement of the vibrational energy. The transducer means is operable at an anti-resonant frequency of the amplifying means so as to act as a high impedance to the vibrational energy. Accordingly, the vibrational energy will flow substantially to the tip portion and provide a localized region of cavitation about the tip portion under varying loads experienced thereby.

In another illustrated embodiment, the asymmetrical step horn portion includes the operative tip, wherein the asymmetrical and symmetrical portions provide a high gain feature for mechanical displacement.

In still another illustrated embodiment, provision is made for an aspiration passage means extending through the tip portion and at least partially through the body portion for allowing aspiration of body tissue into a tip opening in response to a source of vacuum being applied to one end of the passage means.

In another illustrated embodiment, provision is made for passage means having an opening at the distal end of the operative tip portion wherein cavitation produced by the operative tip is localized in a region in the form of generally circular fluidic currents. In this embodiment, the localized region is a few millimeters from the tip opening.

In still another version of the invention there is provided a method of controlling fragmentations of body tissue by controlling the ultrasonic energy applied to the tissue in accordance with steps which can be practiced using the above noted apparatus.

Among the other objects and features of the present invention are provisions of an improved ultrasonic apparatus, the provisions for an improved method and apparatus for enhancing fragmenting efficiency; the provision for an ultrasonic handpiece which has an ultrasonic horn assembly which yields high displacement magnification; the provision for an ultrasonic handpiece which minimizes frictional losses and power consumption; the provision for an ultrasonic handpiece which includes series connected asymmetrical and symmetrical horn portions, wherein one of the horn portions includes a working operative tip; the provision for an ultrasonic handpiece which provides minimal and highly localized cavitation to a working tip thereof; the provision for an ultrasonic handpiece for use in fragmentation and extraction of cataracts; the provision for an ultrasonic handpiece of the above-noted type which provides high displacement but with significantly reduced power; and the provision for an ultrasonic actuator which utilizes high frequency.

Still other objects and further scope of applicability of the present invention will become apparent from the detailed description to follow when taken in conjunction with the accompanying drawings in which like parts are designated by like reference numerals throughout the several views.

DETAILED DESCRIPTION

Figure 1:
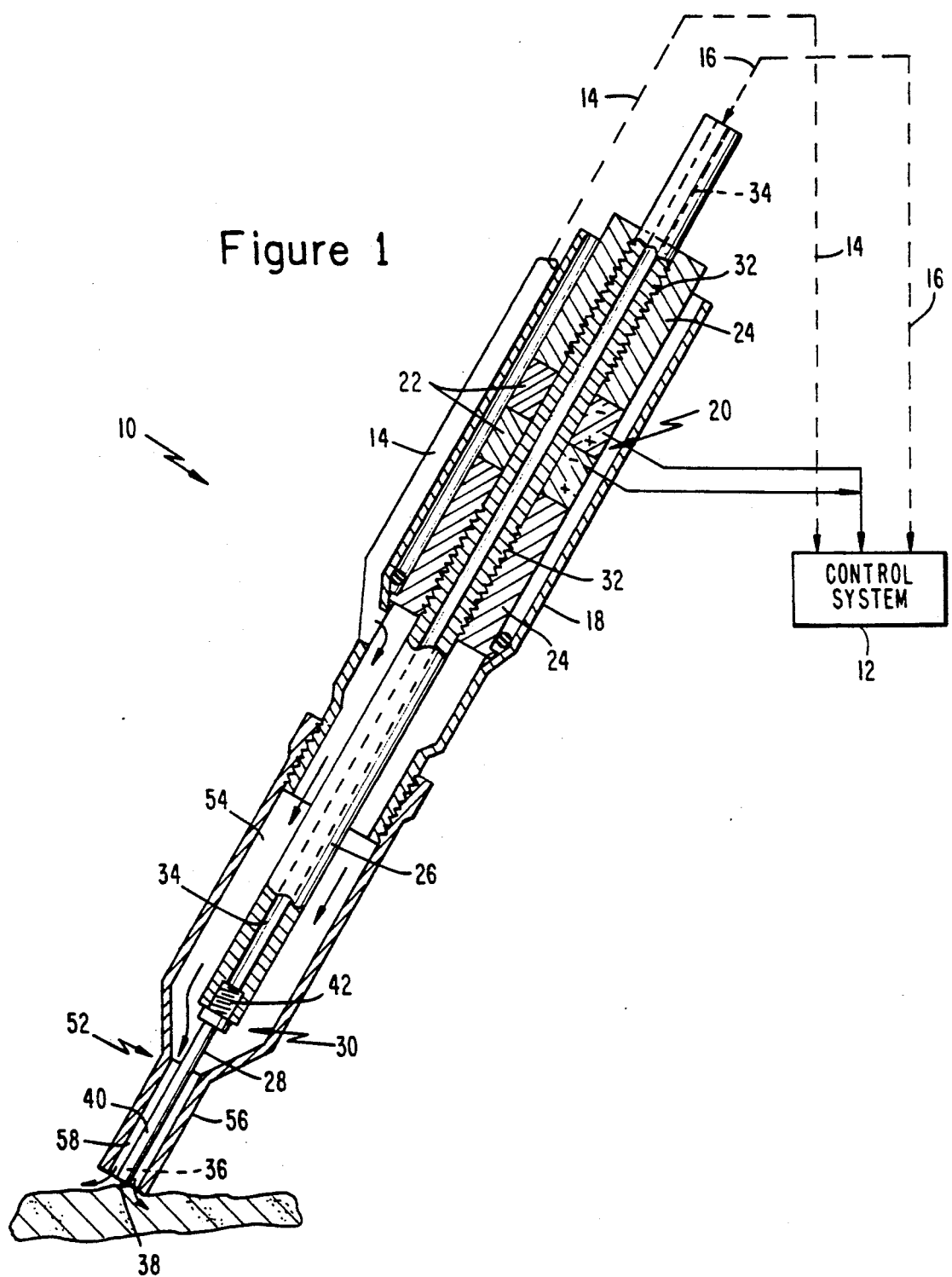
FIG. 1 is a fragmented cross-sectional view of a portion of an ultrasonic surgical apparatus of the present invention.

Reference is made to FIG. 1 for showing an illustrated embodiment of an improved ultrasonically vibrated surgical aspirator apparatus 10 made according to the present invention. The aspiration apparatus 10 is, preferably, adapted for use in precisely removing unwanted body tissue, such as cataractous lens tissue. Ultrasonic surgical apparatus representative of the type to which this embodiment is directed are known and described in U.S. Pat. No. 3,693,613. In this embodiment, the apparatus 10 can be a modified 500 series handpiece and irrigation/aspiration system manufactured by Alcon Surgical of Irvine, Calif.

The ultrasonic surgical apparatus 10 is intended for operation with a control system depicted generally by reference numeral 12. The control system 12 allows control of electrical power through leads L to the ultrasonic surgical apparatus 10. The control system 12 also includes external fluid conduit 14 that is controlled through the system 12 to supply irrigation fluid from a source (not shown) to the ultrasonic aspirator apparatus 10. The control system 12 also includes an aspiration conduit 16 connected to the surgical apparatus 1 for allowing withdrawal of the fragmented tissue particles as well as treatment and body fluids from the operative site. Exemplary of the type of control system contemplated for use with the ultrasonic aspirator apparatus 10 is the 10,000 Series control system manufactured by Alcon Surgical of Irvine, California or that described generally in U.S. Pat. No. 4,713,051. This latter patent is incorporated herein by reference to provide for a more detailed description of the type control system contemplated.

Essentially, the ultrasonic aspirator apparatus 10 includes a handpiece or housing assembly 18 having an outer casing constructed to be held by a surgeon's hand and to isolate the latter from vibrations during use. The handpiece assembly 18 supports and houses an ultrasonic transducer assembly 20. In this embodiment the transducer assembly 20 includes a pair of opposed piezoelectric crystals 22, such as the PZT, which are sandwiched together between a pair of spaced apart and opposing insulated cylindrical transducer end members 24. Basically, the transducer assembly 20 is operable, in response to high frequency electrical energy supplied thereto from the control system 12, under the control of a footswitch or the like. When operated, the transducer assembly 20 produces corresponding high frequency mechanical vibrations which are transmitted in a standing wave-pattern. The transducer assembly 20 is operable to produce ultrasonic vibrations in a range of, for example, 20 kHz to 100 kHz, and, preferably, in a range of about 60 kHz to 80 kHz. Directly and centrally coupled to the transducer assembly 20 is an elongated vibration coupling or transmitting rod 26. The vibration transmitting rod 26 is also coupled to a surgical or operative tip 28 which together define a vibration transmitting or displacement amplifying device 30. The elongated vibration transmitting rod 26 has threaded portions 32 which are threadedly joined to internal threaded portions of the transducer end members 24 as shown in FIG. 1. The vibration transmitting rod 26 is also formed with an aspiration conduit or passage 34 extending along the axial extent thereof. The aspiration passage 34 fluidically interconnects at one end with a central bore 36 of the operative tip 28 and at the other end to the aspiration conduit 16 leading from the handpiece to a suction pump (not shown) associated with the control system 12. Operation of the suction pump causes fragmented body tissue and fluids present at the surgical site to be aspirated through the operative tip 28 and the handpiece assembly 18 to a suitable collection vessel (not shown) associated with the control system 12.

Referring back to the ultrasonic transducer assembly 20 of this embodiment, it generates longitudinal ultrasonic vibrations which are propagated along the vibration transmitting or wave amplification device 30. The propagated vibrational waves have nodal and antinodal points along the standing wave pattern, as seen in FIG. 2C. A vibrational nodal point or node is where there is no vibrational movement. Vibrational displacement and 15 velocity increase from about zero (0) at the nodal points to a maximum at antinodal points. The antinodal points are located midway between adjacent nodal points. It will be appreciated that the nodal points are separated by a vibrational half-wavelength. In accordance with the present embodiment, an antinodal point 35 (FIG. 2C) is located at a point at the distal end segment 38 of the operative tip 28 and a nodal point 35a is located at a proximal end, where there is a threaded junction of the operative tip 28 and the transmitting rod 26.

Another vibrational nodal point 35b (FIG. 2C) is located adjacent the threaded junctions between the vibrational transmitting rod 26 and a transducer end member 24. This latter area of no displacement reduces frictional loses between the threaded portions. Also it serves as a region that the housing assembly 18 is connected thereto as by solder or welding. In this latter regard, the housing assembly 18 will have significantly reduced vibrational energy transmitted thereto.

Figure 2A:
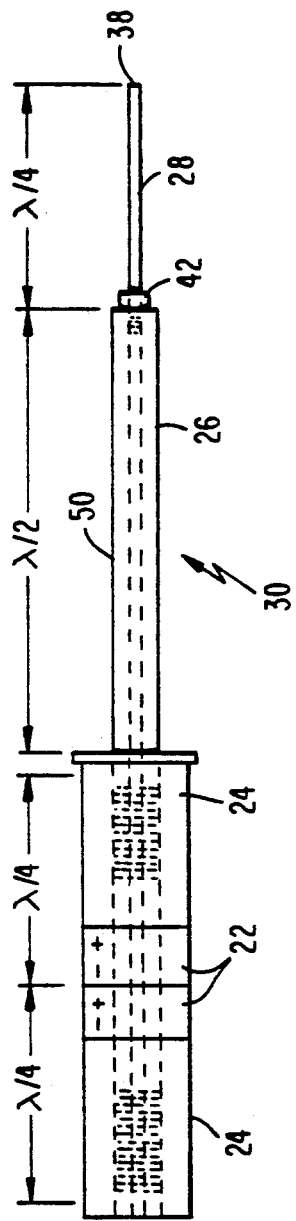
FIG. 2A is an elevational view of one embodiment of a transducer and step horn arrangement of the present invention showing the vibrational wavelength.
Figure 2C:
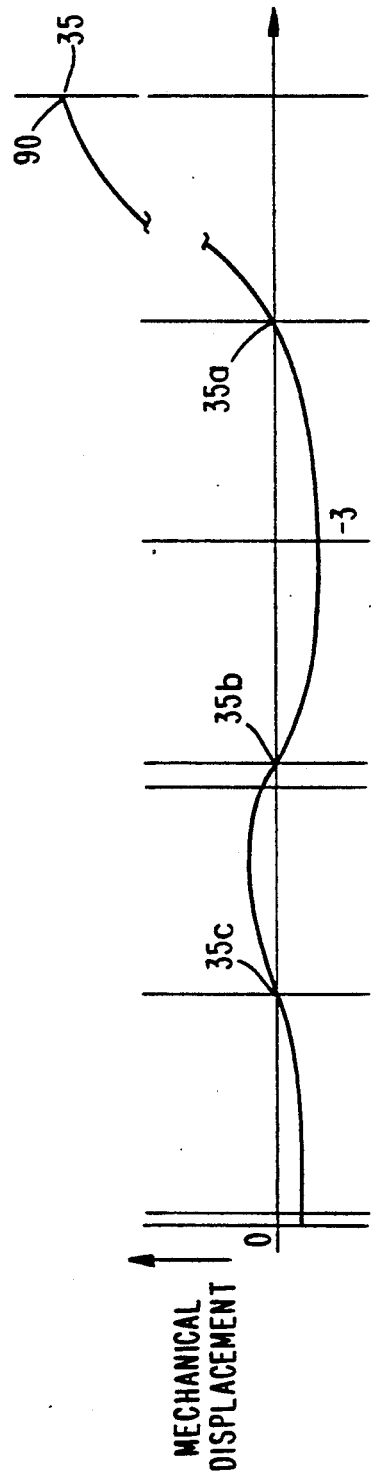
FIG. 2C graphically illustrates vibrational displacement of the surgical apparatus.
Figure 2B:
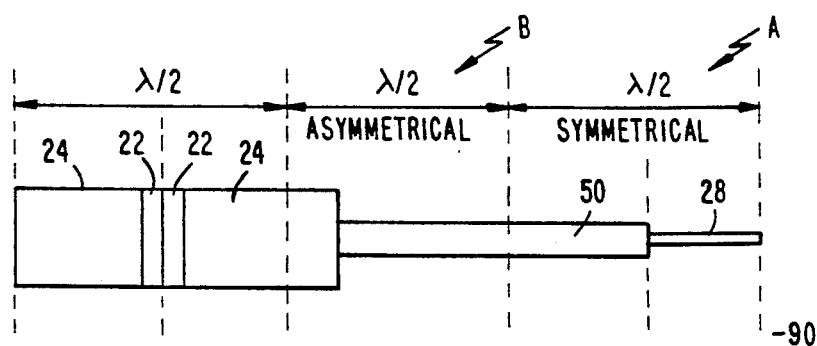
FIG. 2B is a view of the embodiment shown in FIG. 2A, but depicting the half-wavelength step horn portions thereof.
Figure 2D:
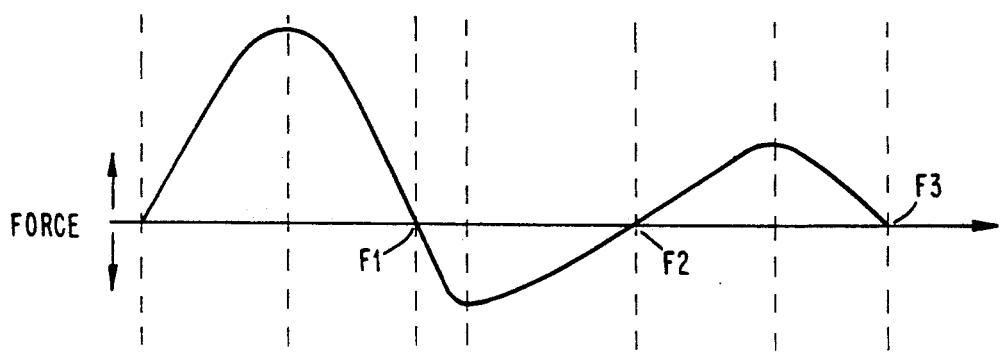
FIG. 2D graphically illustrates the forces of the step horn portions of the surgical apparatus.

FIG. 2B schematically illustrates the handpiece of FIG. 2A, but shows the arrangement of half-wavelength step horns associated therewith. Reference character A of FIG. 2B depicts a symmetrical step horn portion and reference character B shows an asymmetrical step horn portion. The symmetrical portion A includes the operative tip 32 which is a quarter-wavelength resonator. A distinction should be made between FIGS. 2B and 2C. The half-wavelength step portions or resonators of FIG. 2B and the actual vibrational wavelength depicted in FIG. 2C differ in length. In other words, the standing wavelength dimensions of FIG. 2C do not coincide with the actual physical lengths of the half-wavelength resonators or step horns A and B. A half-wavelength resonator can be defined as a single or composite bar which when driven at a certain frequency, called resonant frequency, experiences the following two conditions: the force at both ends is equal to zero and only one node is generated along the bar. In this regard, note FIG. 2D, wherein points of force F1–F3 are depicted. These points are of zero force amplitude and coincide with the respective ends of the symmetrical and asymmetrical horn portions A and B. In FIG. 2B, the symmetrical portion A is made of two quarter-wavelength sections or resonators one of them being the operative tip 28. As seen in FIG. 2A, the operative tip 28 has a narrow cross-sectional area adjacent the distal end segment 38 and a relatively larger threaded portion 42. The operative tip 28 provides a relatively high gain of 30. The member 50 in this embodiment provides a gain of 3. Thus, the total gain of the force amplifying device is about 90.

Referring back to the operative tip 28, it defines, in this embodiment, a quarter-wavelength vibrational transformer. The operative tip 28 includes an elongated and hollow needle portion 40 having a uniform cross-section up to the threaded proximal end or nut portion 42. The operative tip 28 includes a tip opening 44 at its distal end segment 38 through which the fragmented tissue and fluids are aspirated. The materials forming the operative tip 28 can be made of, for instance, titanium or stainless steel. Other materials can be used so long as they have the physical characteristics which allow them to perform the functions contemplated by the invention. In this embodiment, the distal end segment 38 has a maximum displacement and velocity for providing the fragmenting and cavitation for tissue disintegration. The distal end segment 38 is spaced from the nut portion 42 by one-quarter of the vibrational wavelength which is generated. The nut portion 42 can be spaced from the distal end segment 38 by integer multiples of the one-quarter wavelength. The distal end segment 38 of the operative tip 28 is arranged to provide relatively high amplification of the original wave amplitude generated by the transducer assembly as compared to a portion 50 (FIG. 2A) of the rod 26 extending forwardly of the end member 24. Moreover, the transducer assembly 20 provides high frequency in the order of about 60-80 kHz to the vibrating rod 26. It has been determined that this minimizes the likelihood of cavitation of irrigation fluid in contact therewith. The high frequency, in the order noted, increases cutting action and enhances localization of cavitation to generally circular currents around the opening 44. Furthermore, frictional losses and power consumption are minimized by the above construction.

With continued reference to the vibrating transmitting rod the straight ultrasonic horn portion 50 extends between the transducer and member 24 and the operative tip 28. The horn portion 50 is made of suitable materials, such as stainless steel and titanium and have a uniform cross-sectional area. The length of the horn portion 50 is about one-half wavelength. Accordingly, there is provided a node 35b at the threaded section 32. Frictional losses and power consumption are reduced because the node is at this point. The transducer assembly 20 has another node 35c located between the piezoelectric crystals 22 for the same reasons. The combination of the two crystals 22 and end members 24 extends slightly greater than one-half-wavelength. As noted, the transducer assembly 20 is welded or otherwise secured to the housing assembly 18. Moreover, the horn 50 serves as a lossless transmission member which minimizes vibrational gain so that the mechanical displacement at the antinodal points is roughly the same as the transducer assembly 20. Because of this reduced mechanical displacement the heat losses are significantly reduced.

As seen in FIG. 2C, there is little vibrational amplification displacement of the standing wave pattern produced by the transducer assembly 20. However, the operative tip 28 is sufficiently sized and located to produce the necessary gain in vibrational amplification to produce the desired stroke and localized cavitation. The cavitation is in generally circular fluidic currents in a range of from about 0.5 millimeters to 2.0 millimeters from the tip opening 44. The transducer assembly 20 electrically drives the vibration transmitting device a its anti-resonant frequency. Since a quarter-wavelength line is equivalent to a parallel resonant circuit, this presents a very high mechanical impedance to the power source. Thus, the operative tip 28, in effect, is connected to the transducer assembly 20 through a half-wavelength line 50 which is equivalent to a series resonant circuit and has a low impedance. Accordingly, the vibrational energy will flow substantially to the operative tip 28.

Because of the foregoing construction, there are practically no moving parts other than the operative tip 28. Consequently, the temperature of the handpiece assembly 18 is approximately equal to that of the ambient. Thus, cooling of the handpiece assembly 18 is not necessary. Moreover, little power is necessary to maintain a relatively high stroke. Hence, power consumption is low.

Figure 4:
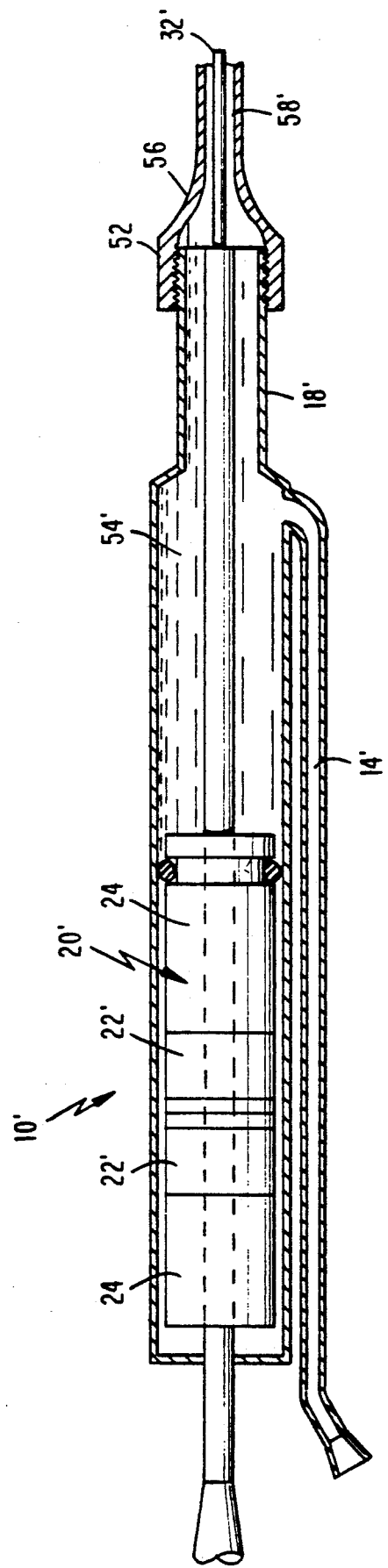

As seen in FIG. 1, surrounding the transducer assembly 20 as well as the vibrating transmitting device 30 is a fluid capacitive sleeve 52. The sleeve 52 is constructed so as to be connected to the housing assembly 18 and provide a irrigation fluid chamber 54 which is sized and constructed in a manner to increase the fluid capacity of the chamber 54. The sleeve 52 has a narrow tip portion 56 which is spaced from the operative tip 18 to define a annular fluid chamber 58 surrounding the tip. It will be appreciated that the irrigation fluid will flow from the chamber 54 to the operative site through the open-ended passage 58. The volume of the handpiece body reservoir or chamber 54 is such that it will act as a fluid accumulator (See FIG. 4) which is placed very close to the irrigation port. It is pointed out that the handpiece having an enlarged fluid chamber is described in detail and claimed in another patent application entitled "Ultrasonic Handpiece Having An Enlarged Fluid Sleeve". It is being described in this invention because it is part of the best mode of the invention being described.

During operation of the ultrasonic aspirator apparatus 10, the operative tip 28 is vibrated for fragmenting the lens into a multitude of small fragments. These tissue fragments are aspirated into the opening 44 of the passage 34 and through the aspiration conduit to a collection device 16. Simultaneously the irrigation fluid travels into the chamber 54 through the annular passageway 58 to the operative site whereat it will be aspirated along with the tissues. The fragmentation of the lens is the result of a cutting action introduced by the vibrating operative tip 28 as well as disruptive cavitation developed by the intense ultrasonic field adjacent to the distal end segment 38. It has been determined that both actions play equally important roles in providing for efficient fragmentation. The highly localized cavitation at the distal end segment 38 of the needle 40 enhances efficient fragmentation, and as noted, reduces the size of the tissue particles entering the aspiration passageway 34. Furthermore, the high frequency vibrations (e.g., 60 kHz-80 kHz) reduce cavitation because the smaller bubbles are formed in which the negative pressure created thereby when collapsing is diminished. This cavitation lessens the tendency to create a longitudinal displacement of the fragmented particles along the operative tip 28 and away from the tip opening 40. According to the present embodiment, with a frequency range of about 60 to 80 kHz the size of the cavitation bubbles produced by the moving nut is small enough not to disturb the surgical view. In addition the vibrational pressure field is low and does not push the fragmented particles away from the tip. Accordingly, there is provided a highly localized cavitation action which provides the kind of swirling action that enhances the fragmentation efficiency of the tool. By virtue of the above construction there is also a significant lowering of the displacement at the point at which the operative tip is connected to the ultrasonic horn portion 50.

Figure 3A:
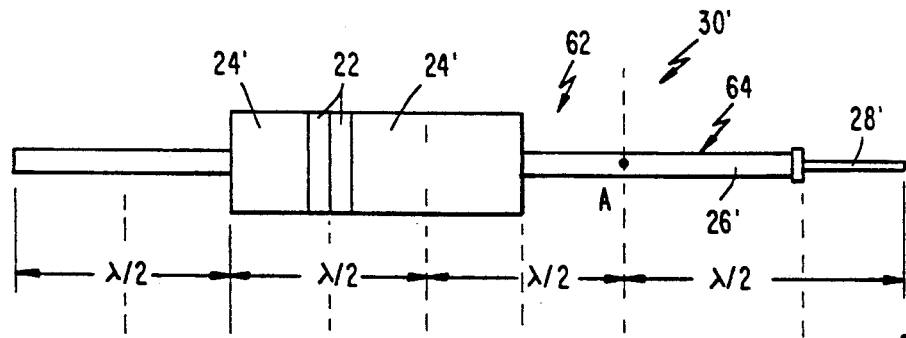
FIG. 3A is an elevational view of another embodiment of the transducer and step horn arrangement of the present invention.
Figure 3B:
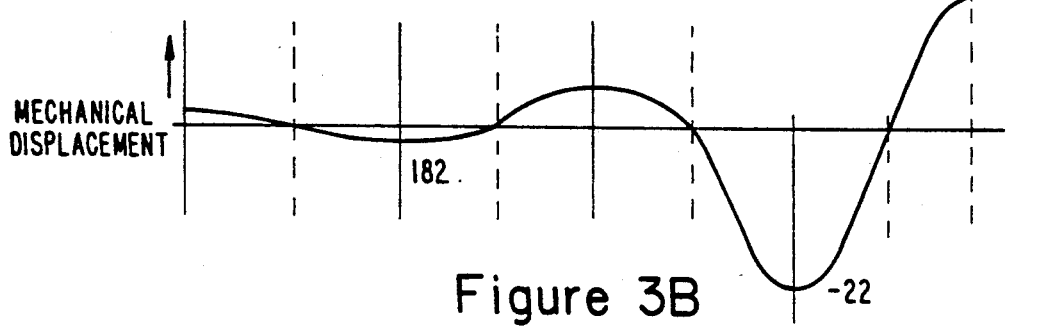
FIG. 3B is a graphical depiction of the vibrational displacement of the embodiment of FIG. 3A; and, FIG. 4 is a cross-sectional schematic view showing the irrigating fluid in the housing assembly.

Reference is now made to FIGS. 3A and 3B which illustrate another embodiment of the present invention. This embodiment differs from the others insofar as the position of the symmetrical and asymmetrical step horns is reversed. The tip 28' is now part of the asymmetrical horn. The construction and operation of the transducer assembly 20' and the vibration transmitting or wave amplifying device 30' are to be housed in a housing assembly (not shown), but like that described above in the previous embodiment.

As shown in FIG. 3A, section 62 is a symmetrical step horn and section 64 is an asymmetrical step horn both tuned on the same frequency. The transducer assembly 20' includes a pair of piezoelectric crystals 22' mounted together on a vibrating transmitting rod 26'. The rear transducer end member 24' is made of stainless steel and the forward transducer end member 24' is made of titanium. The transducer assembly 20' is a half-wavelength resonator and provides a low displacement magnification displacement ratio of about 1.82 (see FIG. 3B). This ratio is the ratio of the specific acoustic impedances of the steel and titanium members 24'. The symmetrical horn portion 60 is made of titanium and has an enlarged cylindrical portion 64 which is an extension of the front transducer end member 24'. The symmetrical horn portion 60 serves to magnify the vibrational displacement of the generated standing wave-pattern as it enters the reduced diameter portion of the transmission rod 26' extending forwardly from the portion 64. There the symmetrical portion 60 provides a desired amplification of displacement in accordance with known formulas. It should be noted that a step horn vibrating in free air is characterized by the following two equations:

$$\sin(ka)\cos(kb) = -(Z_{ob}/Z_{oa})\sin(kb)\cos(ka) \quad (2)$$

$$M = \cos(kb)/\cos(ka) \quad (3)$$

Equation (2) is the frequency equation used to determine the resonant frequencies and equation (3) is the gain equation used to determine the displacement magnification M defined as the ratio of the displacement at the large end to the displacement at the small end.

In such equations, a is the length of the small section, b is the length of the large section, Zob is the characteristic impedance of the large section, Zoa is the characteristic impedance of the small section and k is the wave number. The characteristic impedance $Z_o = \rho cS$ where $\rho$ is the density, c is the sound velocity, S is the cross sectional area and the wave number is $k = 2\pi/\lambda$. It can be shown by combining the above two equations that maximum obtainable magnification is $$M_{max} = Z_{ob}/Z_{oa} \quad (4)$$

which occurs when both sections of the horn are equal to a quarter wavelength. If both sections are made of the same material then M becomes equal to the ratio of the larger cross sectional area to the smaller cross sectional area.

For the case of a symmetrical step horn, both sections have the same length close to a quarter-wavelength, both cosine terms of equation (3) are very small numbers, close to zero. Since the slope of the cosine function is maximum at this point, this type of horn will be very sensitive to changes of the apparent length due to mass loading. For the type of load encountered in cataract fragmentation this will limit the usable gain of a symmetrical horn to about 20.

A substantial improvement is obtained when a step horn including the operative tip is asymmetrical such that neither of the two sections is a quarter-wavelength and the cosine terms are different than zero. In this case the slope of the cosine function has a much lower value than previously and the capability of this horn to maintain a fairly constant displacement under load is improved. However, an asymmetrical step horn will always have a lower magnification than a symmetrical one with the same cross sectional area ratio.

The ultrasonic horn used in the present embodiment is a three step horn made of titanium which is equivalent with a symmetrical and an asymmetrical step horns connected in series. Gain is defined as the ratio of displacement (or velocity) at opposite ends of a given segment of a step horn. In this embodiment, the gain of the symmetrical step horn portion 62 can be 12, wherein the gain for the asymmetrical step horn can be 4 10 with both tuned on the same frequency. It should be noted that the asymmetrical horn includes the ultrasonic tip 28'. The total gain is the product of the two gains, i.e., 48. In this way I combine the high gain feature of a symmetrical step horn with the large bandwidth feature of an asymmetrical horn realizing a horn with high gain and large bandwidth. By bandwidth, it is meant the frequency range within which stroke does not decrease more than 30%. For the amount of load presented by cataracts frequency or voltage compensation are not necessary to achieve fairly constant displacement under load.

The asymmetrical portion 64 provides for further amplification of displacement relative to the symmetrical portion 62 as shown in FIG. 3B. Unlike the previous embodiment, this one is intended to significantly boost the gain of the various sections. The combination of symmetrical and asymmetrical horns provide for high gain for a given volume of metal and more, importantly, a larger bandwidth than the one obtainable with only one symmetrical horn with a similar gain. Accordingly, less power is needed to achieve a desired cutting speed because of the significant gain provided through the combination of symmetrical and asymmetrical horns.

It will be appreciated that less power need be supplied to the transducer assembly 20' to achieve significant displacement magnification of the tip 28'. This provides for an ultrasonic tool which is relatively safer to operate because of the lower electrical voltage needed for operation. The operation of this embodiment is self-evident from the foregoing.

Since certain changes may be made in the above-described methods and apparatus without departing from the scope of the invention herein involved, it is intended that all matter contained in the description or shown in the accompanying drawings shall be interpreted as illustrative and not in a limiting sense.

What is claimed is:

1. An ultrasonic apparatus comprising:
a handpiece assembly;
a power source;
transducer means mounted in said handpiece assembly and being operable for converting electrical power from said power source to ultrasonic mechanical vibrational energy;
motion amplifying means acoustically coupled at one end to said transducer means, said amplifying means including an operative tip portion at another end thereof for contacting body tissue to be removed;
said amplifying means including a symmetrical horn portion comprising a first portion, a second portion and a first step separating said first and said second portions, wherein said first and said second portions are equal in length about said first step and an asymmetrical horn portion comprising a third portion, a fourth portion and a second step separating said third and said fourth portions, wherein said third portion and said fourth portion are unequal in length about said second step, said symmetrical and asymmetrical horn portions being connected in series with each other, said operative tip portion being included as one of said horn portions and being operable for providing a desired degree of displacement at a distal end segment thereof.

2. The apparatus of claim 1 wherein said operative tip is included in said asymmetrical step horn portion; and said symmetrical portion and said asymmetrical portion are sized in a wavelength dimension to provide high gain for mechanical displacement of a distal end segment of said operative tip.

3. The apparatus of claim 1 wherein said operative tip is included in said symmetrical step horn portion;
said symmetrical and asymmetrical horn portions are sized in a wavelength dimension to provide substantially zero displacement at a proximal end segment of said operative tip and maximum displacement at a distal end segment of said tip; and, said transducer means is operable at an anti-resonant frequency of said motion amplifying means so as to act as a high impedance to the vibrational energy, whereby the vibrational energy will flow substantially through said asymmetric horn portion and substantially to said tip to provide a localized region of cavitation about said distal end segment of said tip under varying loads experienced thereby.

4. The apparatus of claim 1 further including an aspiration passage means extending through said tip portion and at least partially through said amplifying means for allowing aspiration of body tissue therethrough in response to a source of vacuum being applied to one end of said passage means.

5. The apparatus of claim 1 wherein said asymmetrical and symmetrical portions are half-wavelength resonators.

6. A method of controlling ultrasonic fragmentation of body tissue comprising the steps of:
providing a handpiece assembly;
providing a power source;
providing transducer means mounted in the handpiece assembly and being operable for converting electrical power from said power source to ultrasonic mechanical vibrational energy;
providing vibrational transmitting means having a body portion with one end acoustically coupled to said transducer means and an operative tip portion at another end thereof for contacting body tissue to be removed;
providing the transmitting means with a symmetrical horn portion comprising a first portion, a second portion and a first step separating said first and said second portions, wherein said first and said second portions are equal in length about said first step combined with an asymmetrical horn portion comprising a third portion, a fourth portion and a second step separating said third and said fourth portion, wherein said third portion and said fourth portion are unequal in length about said second step, said asymmetrical horn portion including said operative tip, wherein the horn portions provide a high gain feature for mechanical displacement;
supplying electrical power to the transducer means for providing preselected displacement of the distal end segment by substantially amplifying displacement of the vibrational energy of the transducer means.

7. A method of controlling the fragmentation of body tissues comprising the steps of:
providing a power source;
providing a handpiece assembly with transducer means mounted in the handpiece assembly and being operable for converting electrical power from said power source to ultrasonic mechanical vibrational energy;

providing motion amplifying means acoustically coupled at one end to the transducer means, the amplifying means including an operative tip portion at another end thereof for contacting body tissue to be removed;

providing the amplifying means with a symmetrical horn portion comprising a first portion, a second portion and a first step separating said first and said second portions, wherein said first and said second portions are equal in length about said first step and an asymmetrical horn portion comprising a third portion, a fourth portion and a second step separating said third and said fourth portions, wherein said third portion and said fourth portion are unequal in length about said second step, said symmetrical and asymmetrical horn portions being connected in series with each other; and, operating the transducer means so that the operative tip portion which is connected to one of the horn portions is operable for providing a desired degree of displacement at a distal end segment thereof.

* * * * *